United States Patent
Cooley

Patent Number: 5,522,402
Date of Patent: Jun. 4, 1996

[54] THREE-DIMENSIONAL SCANNING METHOD FOR DESIGN OF PROTHESES

[76] Inventor: Robert A. Cooley, 4213 Acacia Ave., Bonita, Calif. 91902

[21] Appl. No.: 242,620

[22] Filed: May 13, 1994

[51] Int. Cl.$^6$ ..................... A61B 5/103
[52] U.S. Cl. ..................... 128/782
[58] Field of Search ............. 128/774, 779, 128/782, 664, 665; 33/511, 512, 515

[56] References Cited

U.S. PATENT DOCUMENTS

| | | | |
|---|---|---|---|
| 4,436,684 | 3/1984 | White | 128/774 |
| 4,819,660 | 4/1989 | Smith | 128/774 |
| 4,832,049 | 5/1989 | Matsushita et al. | 128/665 |
| 5,127,420 | 7/1992 | Horvath | 128/782 |

FOREIGN PATENT DOCUMENTS 1683681  10/1991  U.S.S.R. ............. 128/774

*Primary Examiner*—Max Hindenburg
*Attorney, Agent, or Firm*—Brown, Martin Haller & McClain

[57] ABSTRACT

A customized method and apparatus for the design and manufacture of a prosthesis utilizing optical surface mapping of the patient's residuum while the residuum is under pressure; conventional positioning software followed by other conventional software to produce a three dimensional representation; and utilizing conventional CAD/CAM procedures for further design modification and fabrication of the prosthesis. In the preferred embodiment, uniform and non-uniform elevated air pressures are used to simulate the shape that the residuum will take when the patient is walking. To accomplish this the patient's residuum is inserted into a pressure chamber that can be sealed around the patient's upper leg. Alternatively or in combination with the pressure within the chamber, a rubber sock or band may be used to apply pressure to selected areas of the residuum. Also located within the chamber is the equipment used to optically measure the residuum while it is under pressure. The preferred method and apparatus includes the utilization of a pulsed laser ranging system with movable ring mirrors to locate focal points along the residuum for the scan.

21 Claims, 3 Drawing Sheets

THREE-DIMENSIONAL SCANNING METHOD FOR DESIGN OF PROTHESES

BACKGROUND OF THE INVENTION

This invention relates to a method and apparatus for design of a prosthesis using optical surface topography mapping and, more particularly, to a scanning method and apparatus to measure a patient's residuum followed by the use of three-dimensional computer representation to create a three-dimensional design of the prothesis socket and the prosthesis itself.

Currently, the fabrication of most protheses is accomplished by one of two methods. The first method is manual and involves hand casting of the residuum by a skilled prosthetist. The second method involves hand casting of the residuum followed by tactile probe scanning and CAD/CAM (computer-aided design/computer-aided manufacturing) procedures. This method is preferable to the manual method primarily because it limits the fabrication time and results in a more accurate prosthesis fit.

The manual fabrication process normally requires at least 18–20 hours. The hand casting plus CAD/CAM method requires at least five hours. The prosthetist in either case may need to remake the prothesis several times to adjust areas that are uncomfortable to the patient. This occurs more frequently in the manual method.

Often, the fit of a prothesis manufactured under one of the current methods is poor and the prothesis is uncomfortable when the patient is walking because the prothesis has been fabricated from a plaster cast of a relaxed residuum rather than from a partially stressed residuum. Since the residuum is under stress while a patient is walking, it is understandable that a prosthesis designed and manufactured from a plaster cast of a relaxed residuum would produce an uncomfortable and wholly inadequate prosthesis.

SUMMARY OF THE INVENTION

This invention is superior to current prosthesis fabrication techniques because it provides for a method for preparing an optical map of the residuum, directly from the residuum, while the residuum is under pressure. This method eliminates the time and drudgery of using plaster as required by the current techniques and also eliminates the error that inevitably results from measurements taken from a plaster cast rather than directly from the residuum. Additionally, measuring the residuum while under pressure, using both uniform and non-uniform pressures, allows for a superior surface bearing socket, resulting in a better fitting and more comfortable prosthesis. The invention also allows for a less skilled prosthetist to fabricate a suitable prosthesis. Because of the reduction in fabrication time and the ability to employ a less skilled prosthetist, the cost of producing a well fitting prothesis will be lowered considerably.

It is an object of the present invention to scan the residuum using an optical measurement technique such as laser interferometry, holography or other optical surface topography mapping methods as are known in the art. The scan of the residuum is made under elevated uniform and non-uniform pressures in order to cause the residuum to assume the shape that it will take within the socket of the prosthesis when the patient is walking.

In the preferred embodiment, a pulsed laser ranging system is utilized to determine the three-dimensional shape of the residuum. The laser, preferably a class III or weaker power laser, is in a fixed position at the base of a pressure chamber and centered within said chamber. The residuum is inserted into the pressure chamber. Movable mirrors within the chamber are utilized to locate focal points along the residuum. The vertical positioning system is a conical ring mirror, which determines the altitude of the laser and sensing beam. This mirror moves vertically within the chamber, using a motorized screw drive system. Alternatively a pulley system may be utilized. The angular position of the laser beam is determined by a controlled rotating mirror. The case containing the residuum is preferably transparent and is pressurized to a controlled pressure, allowing for determination of the compressibility of different areas of the residuum. In combination with the application of uniform pressure applied via the pressure chamber or in the absence of such application of uniform pressure, non-uniform pressure may also be applied to different areas of the residuum, using a rubber sock or band or another appropriate method of applying pressure to specific areas of the residuum.

This system is applicable to the fabrication of both an above-the-knee and below-the-knee prosthesis, as the entire chamber may be mechanically or manually elevated or, alternatively, the patient may be appropriately positioned to allow for scanning of an above-the-knee residuum.

After the residuum has been scanned and the information digitized, commercial positioning software may be used, followed by the use of other commercial software to convert the measured positions to the three-dimensional image. The three-dimensional image presented on the computer screen may then be modified before sending the information to a numerically controlled milling machine.

An alternative embodiment employs the use of flat mirrors attached to a rotating arm instead of the conical ring mirrors set forth in the preferred embodiment. The vertical positioning is, again, accomplished using a screw drive system or a pulley system.

DETAILED DESCRIPTION OF THE INVENTION

Figure 1:
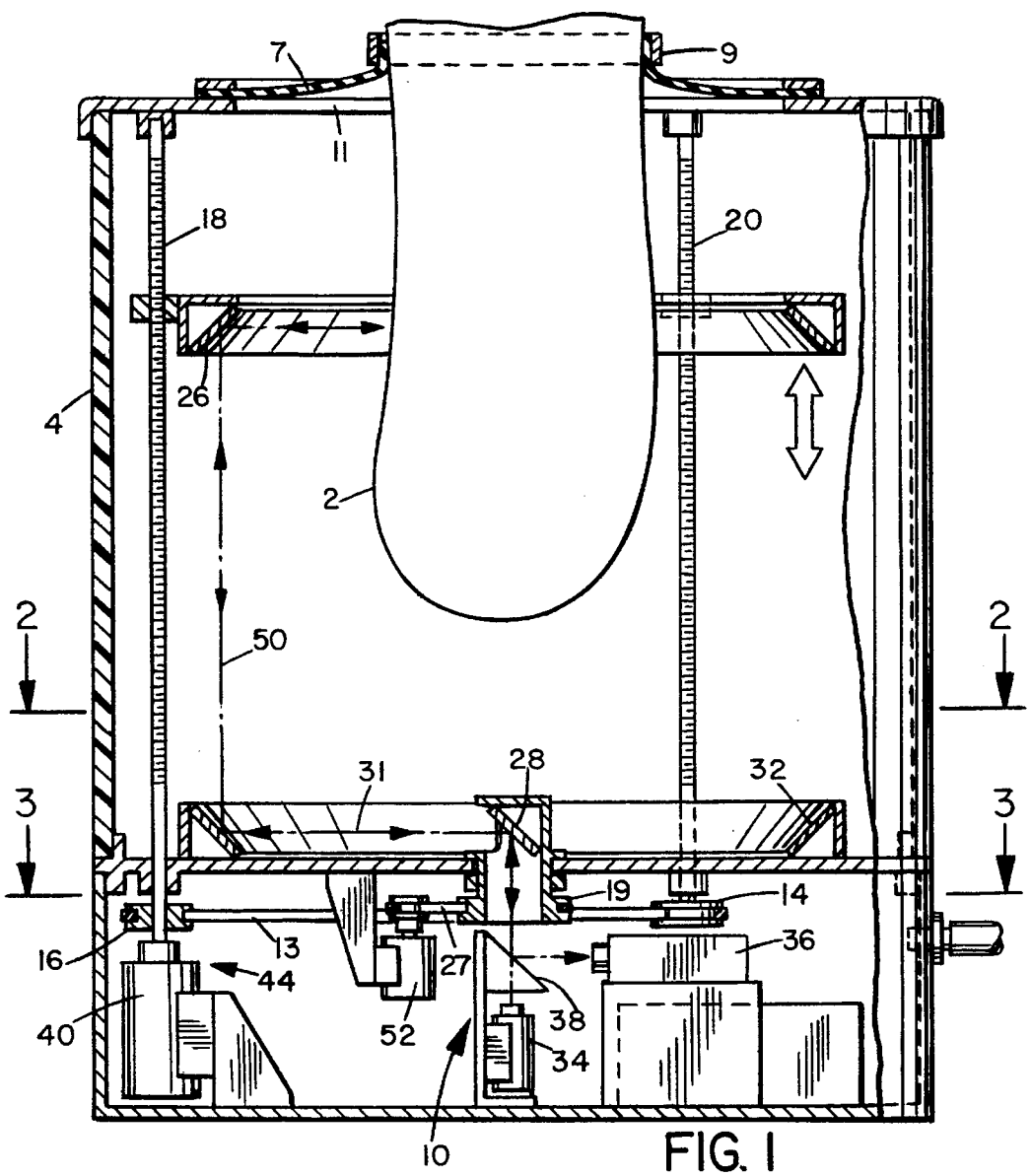
FIG. 1 is a side elevation view, partially cut away, of a preferred configuration of the apparatus.

The preferred embodiment of the invention is as illustrated in FIG. 1. FIG. 1 is a side elevation view, partially cut away, of a preferred configuration of the invention. Contained within and located at the base of transparent cylindrical pressure chamber 4 is a laser pulse forming and ranging system 10. Said laser pulse forming and ranging system may be comprised of commercially available electronics packages. The laser 34 is in a fixed position in the center at the base of the pressure chamber 4. The laser is preferably a class III or weaker power laser to eliminate eye danger. In addition to laser 34, the laser pulse forming and ranging system, consists of a beam splitter 38, a beam rotator mirror 28 and a beam detector 36, as shown in FIG. 1. The beam splitter 38 splits the beam emitted by the laser 34. The beam rotator mirror 28 reflects the beam along path 31 to the fixed full conical ring scan mirror 32. The beam rotation motor 52 along with belt 27 and guide 18 (shown in FIG. 3) rotate the beam rotator mirror 28 to accomplish this. Once the beam hits the sloped surface of the ring scan mirror 32, it travels along path 50 and is further reflected off the elevation determining ring scan mirror 26. The beam is then reflected back from the residuum 2, following the same path 50 and 31 down to beam splitter 38, wherein the initial beam and the reflected beam enter the beam detector 36.

Ring scanning mirror 26 is raised or lowered to allow scanning of the entire length of residuum within chamber 4. Ring scan mirror 26 is raised or lowered utilizing a screw drive system 44. Screw rods 18, 20 and 22 are spaced triangularly and equidistantly apart and are affixed to the base of chamber 4. (Rod 22 is not shown in FIG. 1.) Said rods extend to top of chamber 4. Rods 18, 20 and 22 are each threaded through elevation determining ring scan mirror head 19. Elevation control motor 40 powers screw drive system 44. Inserted into motor 40 is rod 18 upwardly attached to sheave 16. Sheave 16 guides rod 18. Belt 13 is also attached to sheave 12, that guides rod 20.

Seal 7 surrounds residuum 2, and is attached to opening 11. Seal 17 is composed of a flexible inflatable cuff, and may be used in connection with belt 9 to allow chamber 4 to be pressurized.

Figure 2:
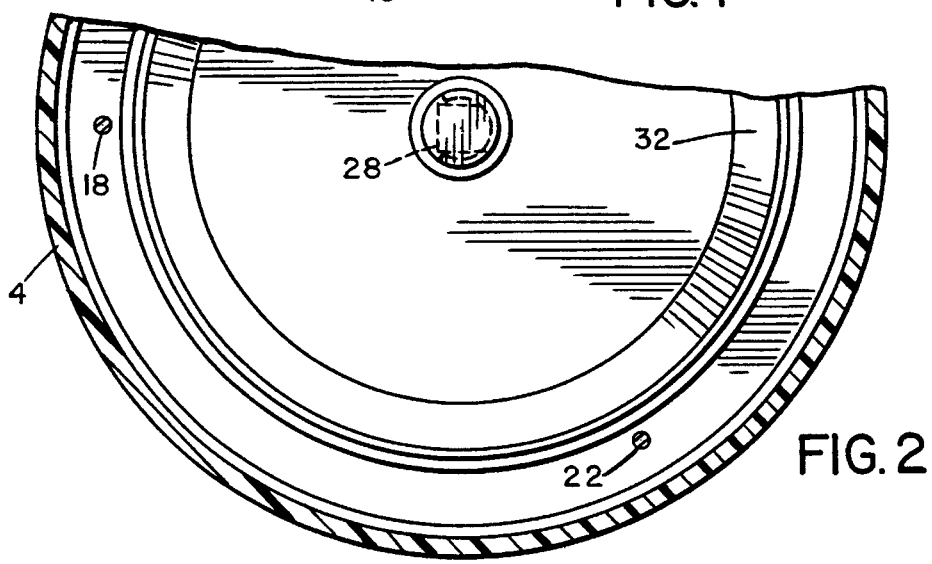
FIG. 2 is a sectional view taken on line 2—2 of FIG. 1.

FIG. 2, a sectional view taken on line 2—2 of FIG. 1, shows chamber 4, rods 18, 20 and 22 (not shown) of screw drive system 44, triangularly spaced equidistant from each other at base of said chamber, along with fixed conical pressure ring scan mirror 32 and beam rotator 28.

Figure 3:
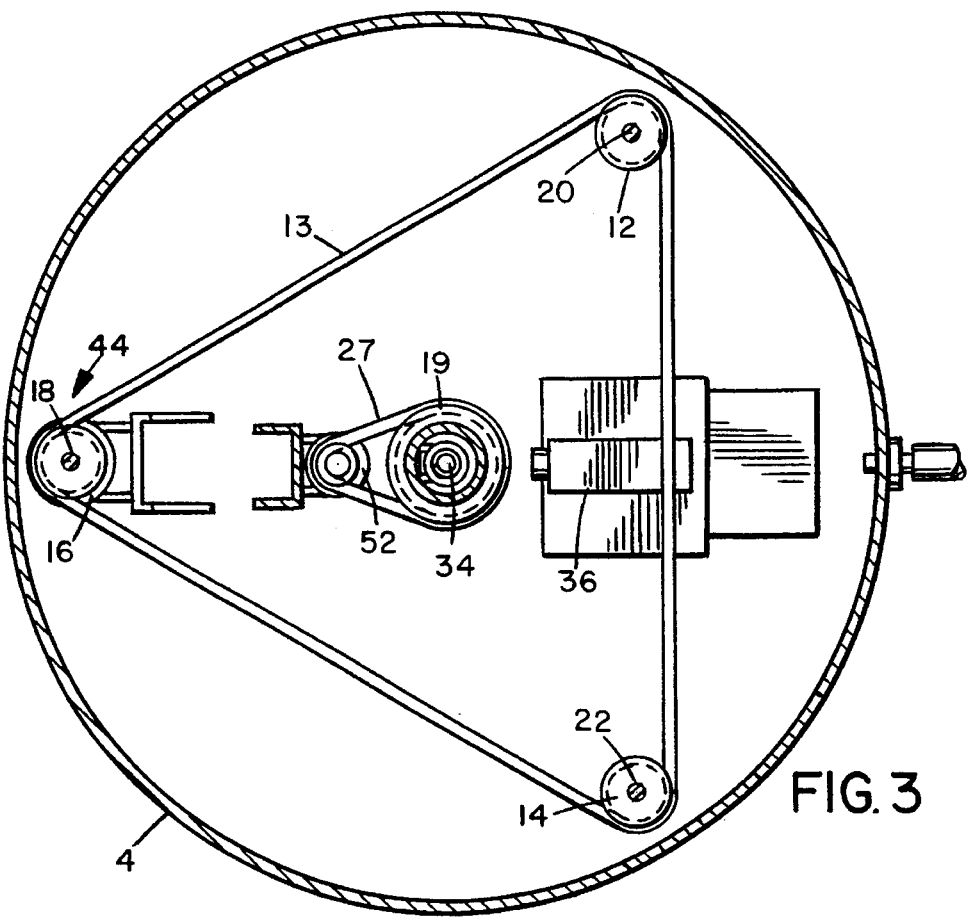
FIG. 3 is a sectional view taken on line 3—3 of FIG. 1.

FIG. 3 is a sectional view taken on line 3—3 of FIG. 1 and again shows fixed screw rods, 18, 20 and 22, triangularly spaced within said chamber and fixed to base of chamber 4. Belt 13 is attached to sheave 12, 14, and 16.

Figure 4:
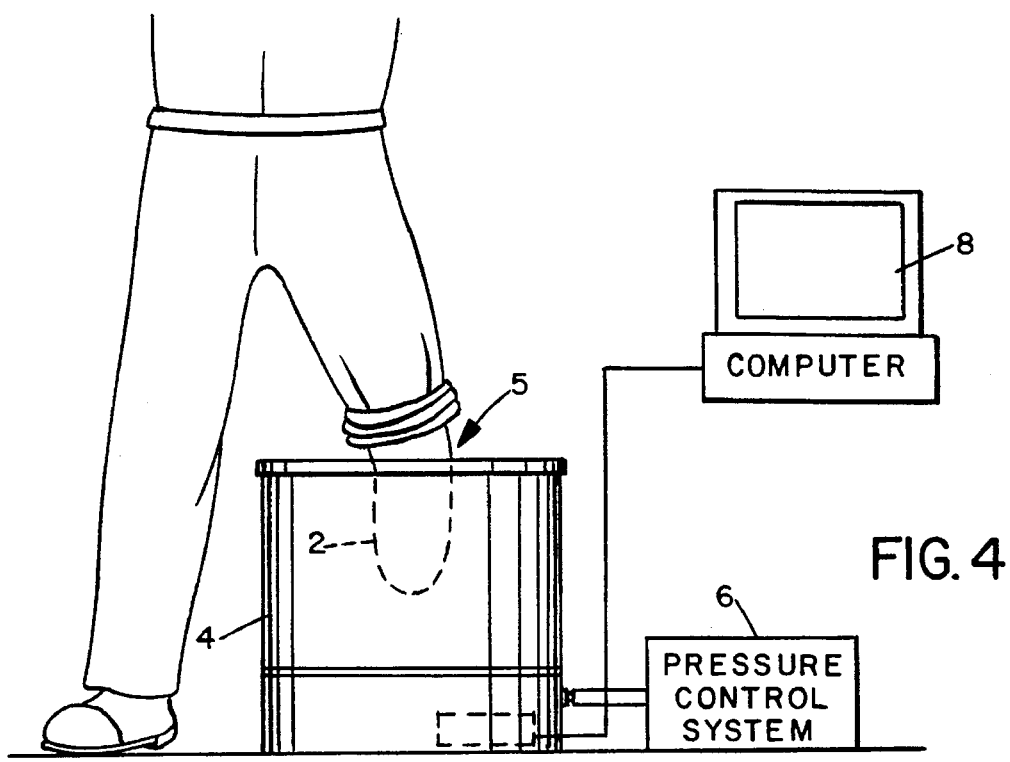
FIG. 4 is a diagrammatic view of the residuum scanning system.

FIG. 4 is a diagrammatic view of the residuum scanning system according to the present invention for fabricating prostheses comprising the steps of scanning 5 a residuum 2 under a controlled pressure 6 and then utilizing conventional CAD/CAM methods to present a three-dimensional representation of the residuum on a computer system and screen 8 for modification prior to manufacture of the prosthesis.

The scanning system 5 preferably consists of optical topography mapping of the residuum, using laser interferometry, holography, and other similar methods as are known in the art. Any other suitable three-dimensional surface topography mapping method may alternatively be utilized.

The pressure control system 6 elevates the pressure within chamber 4. It is preferable to use air to pressurize said chamber; however, other suitable gases may be used for pressurization. The pressure within said chamber is elevated to an optimum pressure, said optimum to be determined. Alternatively or in combination with the pressure chamber a band or rubber sock may be used to apply non-uniform pressures to the residuum during scanning.

The computer 8 is used to present a three-dimensional representation of the residuum which can then be modified and then this information can be sent to a numerically controlled milling machine. Conventional software such as that known as Mathmatica® and conventional data conversion computer interface boards may be used. In the preferred embodiment, surface profile data generated by the ranging system will be directly stored on computer disks in a common CAD importable format such as DXF or SKD files through the use of common off-the-shelf data conversion computer interface boards. The data will later be imported into common CAD systems as streams of points and converted into splines and then into solid surfaces that will define the contours of the scanning image. Once the final image is created for the new file, it will be saved and exported to the milling machine in common IGES or other formats to make the foam or plaster positive. Defining tool paths will be performed at the milling machine as normally performed with computer aided machining.

Figure 5:
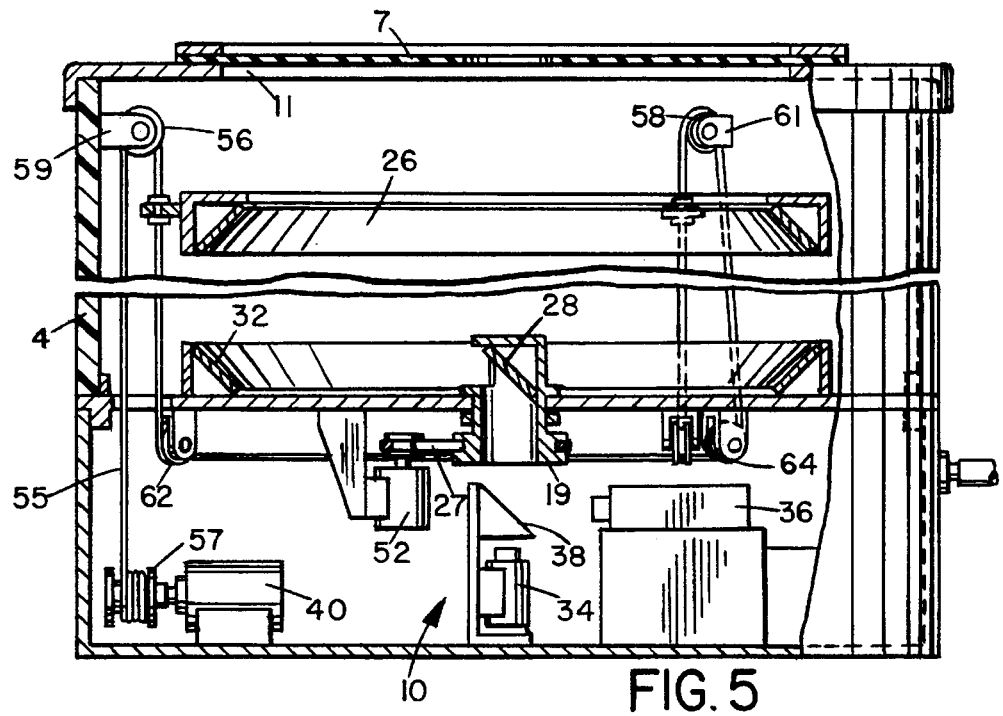
FIG. 5 is a view similar to FIG. 1, showing an alternative vertical scanning drive arrangement.

FIG. 5 is a view similar to FIG. 1, showing an alternative vertical scanning drive arrangement. Elevation control motor 40 is turned on its side and attached to motor with string or band 55 wound around it. Said scanning drive arrangement is further composed of three fixed pulleys 56, 58 and 60 (60 not shown) spaced equidistant from each other and attached to upper sides of chamber 4, using plates 59, 61 and 63 (63 not shown) and movable pulleys 62, 64 and 68 (68 not shown).

Figure 6:
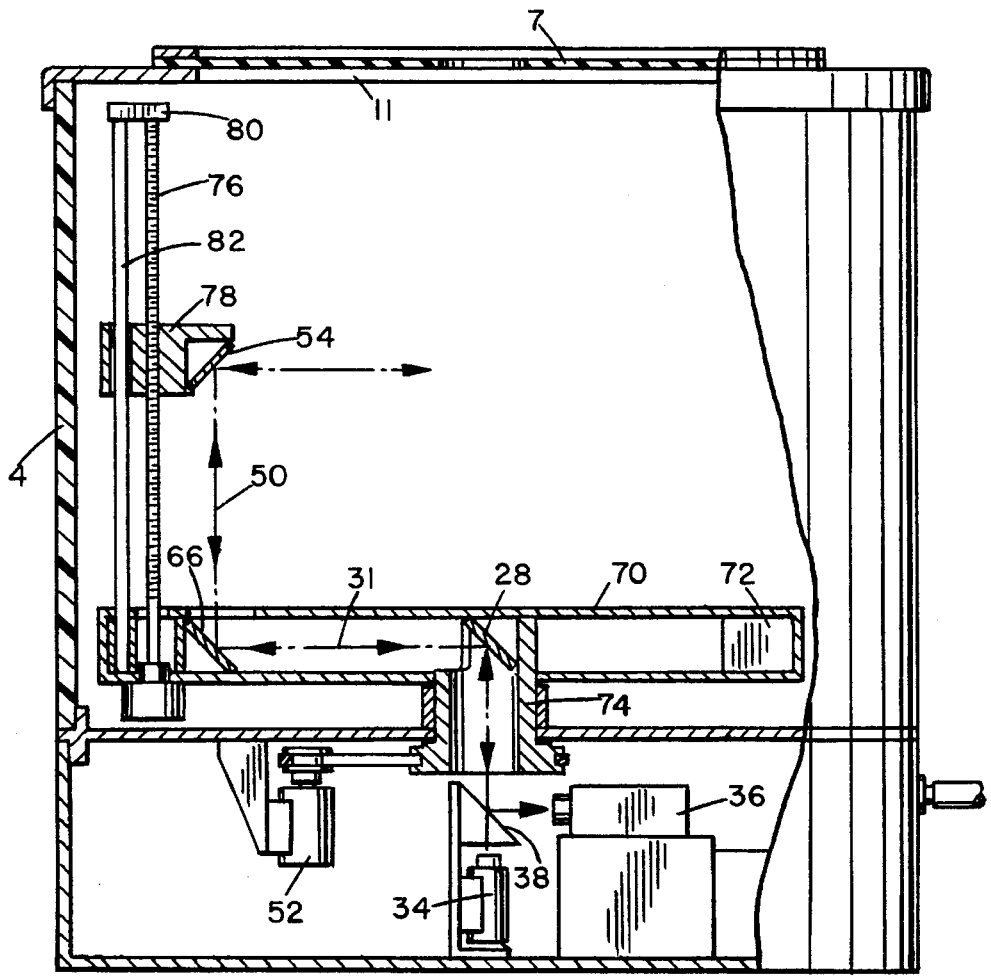
FIG. 6 is a view similar to FIG. 1, showing a rotating scanning arrangement.

FIG. 6 is a view similar to FIG. 1, showing a rotating scanning arrangement. Ring scan mirror 32 shown in FIG. 1 is replaced by flat mirror 66. Ring scan mirror 26, also shown in FIG. 1, is replaced by flat mirror 54. both 66 and 54 are attached to arm 70, having counter balance weight 72. Said arm is fixed to turret 74. The beam emitted from laser 34 follows path 31 and 50 as in FIG. 1. Screw rod 76 is threaded through mirror head 78. Plate 80 fixes rod 76 and guide rod 82 parallel to each other to base of arm 70.

I claim:

1. A method for design of a prosthesis attached to a patient's residuum comprising the steps of:

applying pressure to the residuum using gas;

scanning said residuum using surface topography mapping while said residuum is under selected pressure gradients;

using information from said scanning to design a prosthesis.

2. The method in accordance with claim 1 wherein said applying pressure step further comprises the application of air pressure to the residuum.

3. The method in accordance with claim 1 wherein said scanning step comprises using optical surface topography mapping.

4. The method in accordance with claim 1 wherein said scanning step comprises the use of laser interferometry.

5. The method in accordance with claim 1 wherein said applying pressure to the residuum step further comprises the application of uniform pressure to the residuum to an optimum pressure.

6. The method in accordance with claim 1 wherein said applying pressure to the residuum step further comprises enclosing the residuum within a pressurized chamber.

7. The method in accordance with claim 1 wherein the residuum is subjected to the application of pressure at different points on said residuum using a rubber sock.

8. The method in accordance with claim 1 wherein said the residuum is subjected to application of pressure at different points on said residuum using a rubber band.

9. The method in accordance with claim 1 wherein said pressure chamber utilizes gas pressure.

10. The method in accordance with claim 1 wherein said applying pressure to the residuum step comprises placing the residuum into a pressured chamber that is sealed around said residuum.

11. The method in accordance with claim 10 wherein said seal around said residuum comprises a flexible cuff having a belt.

12. The method in accordance with claim 1 wherein said scanning step comprises a laser pulse forming and ranging system.

13. The method in accordance with claim 1 wherein said scanning step further comprises utilizing movable mirrors to locate focal points along said residuum.

14. The method in accordance with claim 1 wherein said means for using information from said optical surface topography mapping to design a prosthesis comprises using a computer system to present a three-dimensional representation of said residuum.

15. A system for design of a prothesis attached to patient's leg and residuum comprising:

a pressurized container wherein the patient's residuum is inserted;

a surface topography mapping scanner located at the base of said container;

a computer system connected to said scanner, having positioning software and software to produce a three-dimensional image of said residuum.

16. The system in accordance with claim 15 wherein said pressurized container is transparent.

17. The system in accordance with claim 15 wherein said scanner comprises a pulsed laser ranging system.

18. The system in accordance with claim 17 wherein said scanner further comprises:

a fixed conical ring scan mirror;

an elevation determining ring scan mirror; and a motorized screw drive system attached to said elevation determining mirror.

19. The system in accordance with claim 17 wherein said scanner further comprises:

flat mirrors attached to a rotating arm.

20. The system in accordance with claim 17 wherein said scanner further comprises:

a fixed conical ring scan mirror;

an elevation determining ring scan mirror;

a motorized pulley system attached to said elevation determining mirror.

21. The system in accordance with claim 15 wherein said container further comprises:

an inflatable cuff and belt to be attached to the patient's leg above the residuum.

\* \* \* \* \*